(12) United States Patent
Milligan

(10) Patent No.: US 8,439,891 B1
(45) Date of Patent: May 14, 2013

(54) IV START DEVICE AND METHOD

(76) Inventor: Jeane Diane Milligan, Seattle, WA (US)

( * ) Notice: Subject to any disclaimer, the term of this patent is extended or adjusted under 35 U.S.C. 154(b) by 369 days.

(21) Appl. No.: 12/978,110

(22) Filed: Dec. 23, 2010

Related U.S. Application Data

(60) Provisional application No. 61/291,869, filed on Jan. 1, 2010.

(51) Int. Cl.
*A61M 31/00* (2006.01)

(52) U.S. Cl.
USPC .......................................................... 604/512

(58) Field of Classification Search .......... 604/506–508, 604/512, 110, 161, 164.01
See application file for complete search history.

*Primary Examiner* — Kevin C Sirmons
*Assistant Examiner* — Bradley Osinski

(57) ABSTRACT

A method for starting an intravenous fluid line (IV) is disclosed where a combination of a syringe body with hypodermic needle, a dual ampoule with separate reservoirs for bicarbonate and an anesthetic, a trocar and a cannula are configured so that the steps of injecting a wheal of a buffered anesthetic, retracting the needle tip, lancing a vein with the trocar, and withdrawing the trocar tip so that the cannula remains in place in the vein may be accomplished in a single coordinated action by one skilled in the method, such as with one hand while the other hand performs manipulations on the vein and IV site.

7 Claims, 1 Drawing Sheet

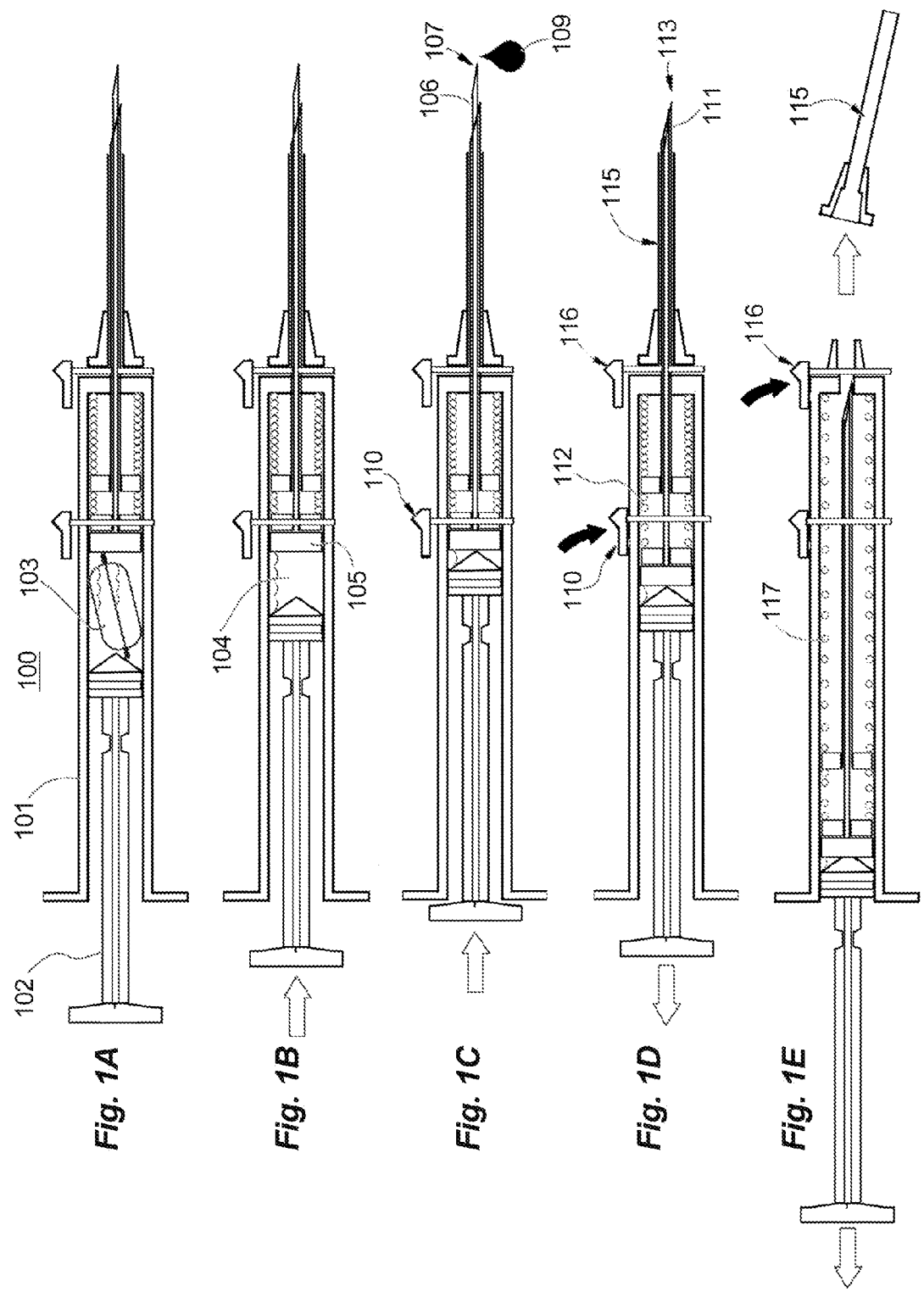

IV START DEVICE AND METHOD

CROSS-REFERENCE TO RELATED APPLICATIONS

This application claims the benefit of 35 U.S.C. §119(e) for priority to U.S. Provisional Patent Application No. 61/291,869 filed Jan. 1, 2010; said priority document being incorporated herein in entirety by reference for all it discloses.

FIELD OF THE INVENTION

This invention relates generally to methods for reducing pain and manipulation when starting medical infusion lines with intravenous cannulas.

BACKGROUND

Intravenous infusion of medication has proved highly effective in treatment of a wide range of clinical conditions, as well as in managing general anaesthesia. Intravenous medications are commonly introduced through an indwelling cannula, most commonly into a peripheral vein, either in combination with a pharmacological acceptable diluent or in alternation therewith. However, the procedure for establishing an intravenous infusion line, more commonly termed an "IV", can be painful, and is sometimes unsuccessful.

Pain continues to be an important factor in the successful placement of the IV. Not uncommonly, patient discomfort can lead to premature withdrawal of the trocar without first establishing patency of venous placement. Thus there is an unmet need to reduce pain associated with starting an IV.

In order to reduce pain when starting an IV, it has been found that subcutaneous administration of a local anaesthetic in advance of the procedure frequently provides relief. A wheal of lidocaine (2-diethylamino-N-[1,6-dimethylphenyl] acetamide), typically administered as a hydrochloride salt, induces field blockage of pain immediately upon administration. Related local anaesthetics, such as described in Goodman's Pharmacological Basis of Therapeutics, may also be used. It is desirable to administer the minimum amount of these substances as needed to achieve the desired effect.

The local anaesthetic can be administered with a very fine needle, such as a 30 gauge needle, in order to further minimize pain. Needles of this size are typically too small, however, for intravenous therapy. So a separate trocar, more commonly 25 to 16 gauge in size, is used to start the IV. Thus the typical procedure requires two separate devices, the first to administer the local anaesthetic and the second to start the IV, leading to delay and complexity, requiring additional supplies and procedures, and is cumbersome.

Formulation of buffered mixtures is further complicated because the most commonly used local anesthetics are unstable when mixed with a buffer such as sodium bicarbonate, unless used promptly. It is known that delay in usage may lead to weakening of the drug, presumably due to decomposition at neutral or near neutral pH.

Ampoules with breakable necks are also known, and may be used to load a lidocaine:buffer mixture at the point of use. However, breakable ampoules are not uncommonly associated with hand injuries due to sharp edges, and the use of two ampoules to prepare a solution at the bedside is complicated and risks contamination. A frangible seal separating two solutions is described in U.S. Pat. No. 5,261,903 to Dhaliwal, which relates to preparation of buffered anaesthetic solutions for local injection. A displaceable bung is also described in U.S. Pat. No. 3,464,414 to Sponnoble. However, these containers pose unrealistic cost and complexity in modern clinical practice, and do not relieve the need for a first device to administer the anaesthetic followed by a second device to start the IV, both of which must be included in the IV kit and handled separately.

Also of concern is safety for the health practitioner. A device for starting an IV typically includes provision for a retractable hypodermic needle, where the sharp end of the needle is urged inside a housing after activation of a spring mechanism by the user. Surprisingly, while sharps are clearly a factor in transmission of blood borne disease, retractable needles have not been associated with higher safety in cannulation procedures, perhaps because of accidental cuts while operating the mechanism or spatter due to motion of spring-loaded parts. Spring-loaded retractable needles have also been associated with decreased success in pediatric patient populations due to accidental premature retraction of the trocar. Retractable needles are described, for example, in U.S. Pat. Nos. 5,195,985, 5,201,719, 5,885,257, 6,210,371, 6,210,375, and 6368303.

An alternative is an extensible sheath, which may be deployed to advance over the trocar on activation of a spring mechanism by the user, such as is described in U.S. Pat. No. 6,685,676. This mechanism is less likely to be associated with blood splatter but is complex to manufacture and operate.

There is also a need in the art for a convenient single-dose syringe or device permitting point of care administration of a buffered anaesthetic subcutaneously prior to the cannulation. Because it is desirable to prepared the buffered anaesthetic solution immediately before or at the time of use, as shown by Dhaliwal (FIG. 4, U.S. Pat. No. 5,261,903) an improved device or method will supply the anaesthetic and buffer separately in an inexpensive container and is configured to mix the two formulations at the time of injection. Globally the market for intravenous cannulas is estimated to be more than one billion dollars annually. Thus, there is a need in the art for a device and method for starting an IV that overcomes the above disadvantages and has other advantages to improve the process of starting an IV.

BRIEF DESCRIPTION OF THE DRAWINGS

The teachings of the present invention can be readily understood by considering the following detailed description in conjunction with the accompanying drawings, in which:

FIGS. 1A through 1E depict steps of a method for starting an IV. In the final step, the soft cannula is released from the trocar and remains in the vein (vein not shown).

SUMMARY

IV therapy is widely used in delivering medications, but pain is a common and undesirable factor in starting an IV and can lead to patient avoidance, trauma, and complications. To reduce pain, prophylactic subcutaneous injection of lidocaine HCl NF has been used. Unfortunately, the low pH of lidocaine HCl is associated with an initial burning sensation, thus diminishing its palliative value. To reduce the pain of injection of lidocaine, it is known to use smaller needles and buffered solutions. But these buffered solutions are very unstable, so the solution must be made shortly before use. In sum, this chain of factors combines to diminish the widespread use of what is an otherwise effective and helpful tool in reducing pain during IV cannulation.

An improved device for starting an IV would be multifunctional, serving 1) for preparation of buffered anaesthetic, 2) for administration of the local anaesthetic, and 3) for inserting the cannula. The device is optionally operable with one hand during the cannulation procedure, requires no assembly for use, includes a safety mechanism for minimizing exposure to sharps.

Similar concerns arise with other local anaesthetics in the same class. The use of a low pH to stabilize lidocaine is also useful in stabilizing combinations of lidocaine with epinephrine, which is used to extend the duration of anaesthesia in other procedures. Other combinations of medications with buffers or medications with other medications can lead to instability of the resultant solution, necessitating use immediately after preparation.

To address these issues, we have devised a method for preparing a mixture of lidocaine and sodium bicarbonate USP in a convenient syringe format. The two solutions are prepared in a double-chambered reservoir. Shattering the reservoir, for example with a plunger of a syringe, releases the liquids and permits mixing so that, for example, a buffered solution of lidocaine can be injected via a needle attached to the syringe.

A fine-gauge hypodermic needle for injection of the buffered mixture of local anesthetic is nested within the bore of a trocar having a large inside diameter. The trocar supports a soft cannula that slides onto the outside surface of the trocar. Thus the device serves multiple functions and its method of use can be described as a series of steps, first injection of the buffered local anesthetic through the smaller needle under the skin near the planned site for insertion of the intravenous cannula, followed by withdrawal of the smaller needle through the trocar, then insertion of the trocar into a vein, followed by withdrawal of the trocar, leaving the soft cannula in the vein.

In a preferred embodiment, the invention is a method for preparing and injecting a mixture of lidocaine and sodium bicarbonate buffer to form a buffered anaesthetic solution during administration and not sooner, preparing the patient by administering the local anaesthetic subcutaneously, and then implanting a soft cannula in a peripheral vein, where the mixing, injecting and implanting is performed with on-board reservoirs for the liquids to be administered and comprising a small needle nested in a trocar, where the cannula is ensheathed on the trocar and the single device is used in consecutive steps to complete the entire procedure. The buffered mixture is preferably at about neutral pH.

Although the following detailed description contains many specific details for the purposes of illustration, one of skill in the art will appreciate that many variations and alterations to the following details are within the scope of the invention. Accordingly, the exemplary embodiments of the invention described below are set forth without any loss of generality to, and without imposing limitations upon, the claimed invention.

DETAILED DESCRIPTION

Definitions

Certain meanings are defined here as intended by the inventors, ie. they are intrinsic meanings. Other words and phrases used here take their meaning as consistent with usage as would be apparent to one skilled in the relevant arts. When cited works are incorporated by reference, any meaning or definition of a word in the reference that conflicts with or narrows the meaning as used here shall be considered idiosyncratic to said reference and shall not supersede the meaning of the word as used in the disclosure herein.

"IV": Intravenous therapy or IV therapy is the giving of liquid substances directly into a vein. It can be intermittent or continuous; continuous administration is called an intravenous drip. The word intravenous simply means "within a vein", but is most commonly used to refer to IV therapy.

Hypodermic needle: as used here, a hollow needle used for delivering a liquid medication subcutaneously. The hypodermic needle is typically a smaller needle used for subcutaneous administration of an anaesthetic. While commonly used with a hypodermic syringe, may also be used with the novel syringes of the invention.

"Cannula" or "catheter": as used here, a slender, hollow, flexible tube for insertion into a vein; typically supported during the insertion procedure by a trocar, which is withdraw after the cannula is seated in the vein.

Trocar: a specialized needle used for supporting a cannula or catheter during the cannulation procedure; a sharp-tipped shaft on which the cannula is supported as a close-fitted sleeve. The trocar is adapted for piercing the epidermis and vascular wall. After cannulation, the trocar is withdrawn.

Syringe: typically referring to a piston-type syringe with plunger and barrel for injecting a liquid, may also refer to the novel syringes of the invention. Optionally a syringe is fitted at the injection tip with a detachable and interchangeable hypodermic needle. The syringes of the invention may include integral, non-detachable hypodermic needles.

Unless the context requires otherwise, throughout the specification and claims which follow, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. The appended claims are not to be interpreted as including means-plus-function limitations, unless such a limitation is explicitly recited in a given claim using the phrase "means for." Furthermore, the particular features, structures, or characteristics may be combined in any suitable manner in one or more embodiments. Therefore, the scope of the present invention should be determined not with reference to the above description but should, instead, be determined with reference to the appended claims, along with their full scope of equivalents.

DRAWINGS

In a first embodiment, the invention utilizes a hypodermic needle to administer an anaesthetic mixture and a trocar to implant an intravenous soft cannula, where the needle, trocar and cannula are coaxially nested. In a second embodiment, an extensible safety sheath is also provided. While the explanation and description shown herein is generally directed at administration of a lidocaine/bicarbonate buffered mixture and subsequent steps of starting an IV, the invention is not necessarily limited thereto, and may also encompass a novel syringe dosing system for administering a therapeutic mixture where the mixture is made during the injection, or where the composition of the mixture is made during the injection with a fixed proportion.

By a first manufacturer, a duplex ampoule is realized by encapsulation of a first liquid in a first reservoir and a second liquid in a second reservoir where the two reservoirs are frangible and are separated by an intermediate frangible film therebetween. The reservoirs are cup shaped and are optionally formed by vacuum molding. Once filled, the first reservoir is covered by the intermediate layer and sealed and the subassembly containing the first fluid is then inverted and placed over the second reservoir after filling the second fluid. The entire assembly is then sealed around the edges and any flash removed. While glass may be used for making duplex ampoules of this kind, a preferred material is a highly brittle shatter-prone plastic such as a polystyrene, polymethyl methacrylate, acrylonitrile-styrene and the like, such materials typically having high crystallinity and low ductility. These materials are prone to fracture under strain and fragment rather than fold. Their toughness can be adjusted by blending for example with polypropylene, polyethylene terephthalate, polylactams, and so forth, as is known in the art. By scoring or etching lines in the material, yield points can be prestressed. Ultrasonic welding is sufficient to form suitable seals. Materials are chosen for compatibility with the liquid to be contained therein. By a second manufacturer, a blow-fill-seal process to form a duplex ampoule is accomplished in a single step.

To assemble the device, the plunger, duplex ampoule, and filter pad may be viewed as a first cluster, the hypodermic needle, mounted in a slidable sealing disk, latch release and short coil spring are a second cluster, and the trocar with second slidable sealing disk and associated long coil spring, form a third cluster, where the three clusters are inserted into the syringe barrel starting with the third cluster so that the hypodermic needle inserts through the inside diameter of the trocar and the needle end protrudes from the tip of the device. The second triggering latch is used to affix the trocar in place, holding the long spring in compression. The cannula is then slipped over the trocar and secured on the nose of the syringe barrel.

As shown in FIG. 1, starting an IV is executed by a series of steps. In FIG. 1A, the preloaded device 100, such as would be provided with a kit for starting an IV, is ready for use. The device comprises a syringe-like body with syringe barrel 101 and piston 102 and a duplex ampoule 103 disposed in the syringe barrel.

In FIG. 1B, the duplex ampoule 103 is shattered, releasing the anaesthetic and the buffered solution, thereby forming an injectable mixture 104. This may be accomplished by pressure on the syringe piston in its barrel. Continued pressure on the syringe piston, as shown in FIG. 1C, forces the buffered mixture through a filter 105, into the hypodermic needle 106 and out the needle tip 107. It is in this step that a subcutaneous wheal of local anaesthetic is injected at the site where the IV will be placed, as indicated for illustration by droplet of fluid 109. Then, using the first release latch (110, first black arrow, FIG. 1D), the hypodermic syringe is withdrawn into the trocar 111. A shorter spring member 112, which was under compression, urges the needle back inside the barrel of the syringe when the latch is released, withdrawing the needle tip inside the trocar. The exposed lancing tip 113 of the trocar is then used to insert the ensheathed cannula 115 into the vein (not shown) and the trocar is withdrawn. By pressing the second release latch (116, second black arrow, FIG. 1E), the trocar is retracted within the body of the syringe barrel. A longer spring member 117, which was under compression, urges the trocar to retract into the barrel housing of the syringe body. The cannula 115 remains in the vein.

Advantageously, the method minimizes pain to the subject in need of IV therapy. Yet more advantageously, in the hands of a skilled user the method for starting an IV may be accomplished with one hand while the other hand performs manipulations on the vein and IV site.

Additional steps for attaching an IV fluid to the cannula are accomplished as is generally known to one skilled in the art.

A device for the method and instructions for its use are provided by a manufacturer. Thus the method can be characterized as having the steps of:
providing a device having
i) a first reservoir of a local anaesthetic and a second reservoir of a buffer, wherein the reservoir is disposed within a body of a syringe, the syringe with piston and barrel;
ii) a hypodermic needle having a first outside diameter, a fluid receiving end and a needle tip;
iii) a trocar having an inside diameter incrementally greater than the first outside diameter of the hypodermic needle, the trocar having a lancing tip;
iv) a cannula having an inside diameter configured for slidably fitting over the trocar and detachably attaching to an adaptor on the barrel;
wherein the hypodermic needle is coaxially nested inside the trocar with the needle tip projecting anteriorly therefrom and slidingly retractable therethrough, and the trocar is coaxially nested inside the cannula with the lancing tip projecting anteriorly therefrom and slidingly retractable therethrough; and,
providing instructions to
a) first mix the local anaesthetic and the buffer, thereby forming a buffered anaesthetic mixture;
b) then insert the needle tip under the skin of a subject in need of an IV and, using the plunger, inject via the fluid receiving end a wheal of the buffered anaesthetic mixture thereunder;
c) then slidingly retract the needle tip of the hypodermic needle into the trocar, thereby enclosing the needle tip;
d) then insert the lancing tip of the trocar into a vein at an IV site selected on the subject in proximity to the wheal, the wheal for anesthetizing the IV site;
e) detaching the cannula from the syringe and withdrawing the trocar from the vein, while leaving the cannula in place; and
f) slidingly retracting the trocar into the body of the syringe, thereby enclosing the lancing tip. The method generally also includes steps for secure the cannula to the IV site and for attaching an IV fluid reservoir to the cannula. The instructions generally also include a step for disposing of the syringe body with internally retracted sharps, i.e. both the needle tip of the hypodermic needle and the lancing tip of the trocar are safely retracted inside the barrel of the syringe so as to minimize risk to personnel handling the used device.

All publications and patent documents cited in the specification and in any accompanying information disclosure statement are hereby incorporated by reference in their entirety as may be useful to the understanding of the invention. Although the foregoing invention has been described in some detail by way of illustration, explanation and example, it will be obvious to one skilled in the art that certain changes or modifications may be practiced within the scope of the claims. Therefore, the invention is not to be limited to any one particular embodiment or combination of embodiments disclosed here, but the scope of the appended claims is to be construed as broadly as permitted by law.

I claim:

1. A method for starting an IV in a peripheral vein, which comprises
providing a device having
i) a first reservoir of a local anaesthetic and a second reservoir of a buffer, wherein said reservoir is disposed within a body of a syringe, said syringe with piston and barrel;

ii) a hypodermic needle having a first outside diameter, a fluid receiving end and a needle tip;

iii) a trocar having an inside diameter incrementally greater than said first outside diameter of said hypodermic needle, said trocar having a lancing tip;

iv) a cannula having an inside diameter configured for slidably fitting over said trocar and detachably attaching to an adaptor on said barrel;

wherein said hypodermic needle is coaxially nested inside said trocar with said needle tip projecting anteriorly therefrom and slidingly retractable therethrough, and said trocar is coaxially nested inside said cannula with said lancing tip projecting anteriorly therefrom and slidingly retractable therethrough; and, providing instructions to a) first mix said local anaesthetic and said buffer, thereby forming a buffered anaesthetic mixture;

b) then insert said needle tip under the skin of a subject in need of an IV and, using said plunger, inject via said fluid receiving end a wheal of said buffered anaesthetic mixture thereunder;

c) then slidingly retract said needle tip of said hypodermic needle into said trocar, thereby enclosing said needle tip;

d) then insert said lancing tip of said trocar into a vein at an IV site selected on said subject in proximity to said wheal, said wheal for anesthetizing said IV site;

e) detaching said cannula from said syringe and withdrawing said trocar from said vein, while leaving said cannula in place; and f) slidingly retracting said trocar into said body of said syringe, thereby enclosing said lancing tip.

2. The method of claim 1, which further comprises an instruction for safely disposing of said syringe body with retracted sharps.

3. The method of claim 1, which further comprises an instruction to secure the cannula to the IV site and attach an IV fluid to said cannula and administering said IV fluid via said vein.

4. The method of claim 1, where said step for triggeredly retracting said hypodermic needle comprises actuating a nested spring-loaded mechanism with trigger for actuating same.

5. The method of claim 1, where said step for triggeredly retracting said trocar comprises actuating a nested spring-loaded mechanism with trigger for actuating same.

6. The method of claim 1, wherein said first reservoir and said second reservoir are formed by a process of blow fill molding in a frangible duplex ampoule.

7. The method of claim 1, wherein said steps a)-f) are optionally accomplished with one hand while the other hand performs manipulations on the vein and IV site.

\* \* \* \* \*